United States Patent [19]

Chevremont et al.

[11] Patent Number: 5,847,124
[45] Date of Patent: Dec. 8, 1998

[54] HYDRATED FORMS OF ZILPATHEROL HYDROCHLORIDE

[75] Inventors: Yves Chevremont, Villeneuve Sous Dammartin; Jean-Yves Godard, Le Raincy, both of France

[73] Assignee: Roussel Uclaf, France

[21] Appl. No.: 989,223

[22] Filed: Dec. 11, 1997

Related U.S. Application Data

[62] Division of Ser. No. 659,367, Jun. 6, 1996, Pat. No. 5,731,028.

[30] Foreign Application Priority Data

Jun. 13, 1995 [FR] France ................................ 95 06966

[51] Int. Cl.⁶ .................................................. C07D 487/04
[52] U.S. Cl. .............................................................. 540/579
[58] Field of Search ............................................... 540/579

[56] References Cited

U.S. PATENT DOCUMENTS

| | | | |
|---|---|---|---|
| 4,585,770 | 4/1986 | Frechet et al. | 514/214 |
| 5,015,639 | 5/1991 | Berger et al. | 514/213 |
| 5,629,308 | 5/1997 | Janssens et al. | 514/214 |

*Primary Examiner*—Mukund J. Shah
*Assistant Examiner*—Ann M. Kessinger
*Attorney, Agent, or Firm*—Bierman, Muserlian and Lucas

[57] ABSTRACT

Crystallized anhydrous zilpaterol hydrochloride having less than 5% of the crystals with a size of less than 15 microns and at least 95% of the crystals having a size of less than 250 microns and a process for its preparation and novel intermediates.

1 Claim, No Drawings

_(5,847,124)_

HYDRATED FORMS OF ZILPATHEROL HYDROCHLORIDE

PRIOR APPLICATION

This application is a division of U.S. patent application Ser. No. 659,367 filed Jun. 6, 1996, now U.S. Pat. No. 5,731,028.

STATE OF THE ART

French Patent No. 2,608,046 describes the use of zilpaterol hydrochloride to increase the weight of breeding animals such as bovines and pigs and to improve the quality of their meat. Zilpaterol hydrochloride can be added to the animal feed directly or can be prepared as a premix which is then incorporated into the animal feed.

An example of a suitable premix is described in European Patent application No. 197,188 which consists of sticking the active principle to corn cobs in which the active ingredient particle size must be smaller than the support particles.

For sticking on corn cobs which have a size of between 300 to 800 microns, it is desirable that all of the particles of active ingredient have a size of less than 300 microns and that the majority have a size of between 50 to 200 microns. It is also desirable that the particles of active ingredient are not too fine if it is desired to avoid problems of dust. When the particles of active ingredient are too fine and appear in the form of dust, there is a hygiene problem for the users who may be irritated, even poisoned, for example when the active ingredient penetrates into the pulmonary alveoli. There are also serious problems for the environment.

OBJECTS OF THE INVENTION

It is an object of the invention to provide a specific crystallized form of zilpaterol hydrochloride and a process and intermediates for its preparation.

It is another object of the invention to provide an improved animal feed and a method of increasing the weight and meat quality of breeding animals.

These and other objects and advantages of the invention will become obvious from the following detailed description.

THE INVENTION

The novel product of the invention is crystallized anhydrous zilpaterol hydrochloride having less than 5% of the crystals with a size of less than 15 microns and at least 95% of the crystals having a size of less than 250 microns. The product has the advantage of being dust-free and is a form useful for increasing the weight of breeding animals and the quality of their meat.

The novel intermediates of the invention are zilpaterol hydrochloride monohydrate and zilpaterol hydrochloride trihydrate.

The novel process of the invention for the preparation of crystallized anhydrous zilpaterol hydrochloride comprises forming a supersaturated solution of zilpaterol hydrochloride in water or aqueous ethanol at a temperature greater than 50° C., cooling the said supersaturated solution to effect crystallization of zilpaterol hydrochloride monohydrate, cooling the solution below 20° C. to effect crystallization of zilpaterol hydrochloride trihydrate and drying the hydrated crystals to obtain the desired product.

In a variation of the process of the invention, zilpaterol hydrochloride is dissolved in a minimum of water at 60° to 100° C., pouring the resulting solution into a saturated solution of zilpaterol hydrochloride in aqueous ethanol, seeding the mixture with zilpaterol hydrochloride trihydrate crystals while stirring at a temperature below 20° C. and drying the resulting zilpaterol hydrochloride trihydrate crystals.

In another variation of the process of the invention, the process comprises forming a saturated aqueous solution of zilpaterol hydrochloride by dissolving anhydrous zilpaterol hydrochloride in water at a temperature of less than 30° C. whereby zilpaterol hydrochloride trihydrate spontaneously cristallizes and drying the said trihydrate crystals to obtain the desired product.

The novel method of the invention for increasing the weight of breeding animals and improving the quality of their meat comprises incorporating into the animal feed an effective amount of the crystallized anhydrous zilpaterol hydrochloride sufficient to increase the body weight and improve the quality of the meat. The product may be added directly to the animal feed or as a premix supported on an inert carrier such as ground corn cobs.

In the following examples, there are described several preferred embodiments to illustrate the invention. However, it is to be understood that the invention is not intended to be limited to the specific embodiments.

Preparation 1

400 g of zilpaterol hydrochloride, 480 ml of water and 240 ml of ethanol were introduced into a reactor all at once and the suspension was heated to 70° C. After 15 minutes, total dissolution was obtained and the solution was cooled to 45° C., maintained there for 30 minutes from the start of the crystallization of the monohydrate form. The needle-shaped crystallization, characteristic of the monohydrate, was verified by simple examination with an optical microscope. The suspension was then steadily cooled to 10° C. over 35 minutes and the thick suspension obtained was seeded with 0.2 g of the micronized trihydrate form ($H_2O$=13%, 97% of particles<10$\mu$).

The suspension was stirred at 10° C. until the conversion of the monohydrate form into the trihydrate form had finished and the granular crystallization and the absence of needle-shaped crystals was verified using an optical microscope. The duration of the conversion varied from 5 to 17 hours. The suspension was heated to 30° C. for 16 hours and then steadily cooled to 0° C. over 2 hours. After a contact of 2 hours at 0° C., the product was separated and washed with 100 ml of water with 33% of ethanol. The crystals were dried for 16 hours at 20° C. under reduced pressure (15 torr), then at 60° C. for 24 hours still under reduced pressure in the presence of potassium in pellet form. The dry product was then passed through a sieve of 0.6 mm to obtain 358 g of micro-crystallized zilpaterol hydrochloride (water=0.4%, ethanol=0.05%, size of particles: 3%<15$\mu$, 93%<200$\mu$, 100%<245$\mu$).

Preparation 2

200 ml of water were introduced into a reactor and heated to 30° C. and 160 g of anhydrous zilpaterol hydrochloride in stick form were added rapidly. Almost total dissolution was achieved and after about 10 minutes, crystallization developed spontaneously. Observation of the crystals under an optical microscope showed that it was indeed the trihydrated form (crystals of granular form). After ninety minutes of contact at 30° C., the suspension was steadily cooled to 0° C. over one hour and then stirred for 2 hours at 0° C. The product was separated and the mother liquors were displaced by washing with 40 ml of water. The product was dried under the conditions of Preparation 1 to obtain 144 g of micro-crystallized zilpaterol hydrochloride which was sieved over a stainless steel sieve set placed on a three dimensional vibrator to obtain 137 g from the oversize products of sieving at 50$\mu$ (water=0.65%, size of particles: 1%<15$\mu$, 92%<200$\mu$, 99%<250$\mu$).

Preparation 3

30 g of zilpaterol hydrochloride in a reactor were dissolved in 300 ml of ethanol with 50% of water and the solution was cooled down to +15° C. and seeded with 4 g of crushed trihydrate (H$_2$O=11.8%, size of particles: 60%<50μ). A solution of 210 g of zilpaterol hydrochloride in 300 ml of ethanol with 50% of water maintained at about 85° C. was added steadily over 3 hours with stirring at +15° C. Then, the suspension was heated to +27° C. and stirred for 20 hours at 27° C. Then, this suspension was steadily cooled to 0° C. over 90 minutes and the mixture was stirred at 0° C. for 2 hours. The suspension was separated and the mother liquors were displaced at 0° C. with 80 ml of ethanol with 50% of water. The isolated crystals were dried under reduced pressure under the conditions of Preparation 1 to obtain 215 g of micro-crystallized zilpaterol hydrochloride (water=1.3%, size of particles: 4%<15μ, 90%<200μ, 99%<250μ).

Infrared Spectrum

TABLE 1

The characteristic bands of each polymorph were as follows:

| Form | Anhydrous | Monohydrate | Trihydrate |
|---|---|---|---|
| Wave number of the characteristic band (cm$^{-1}$) | 3280 | 3380 | 3470 |
| | 3180 | 3230 | 3350 |
| | 1705 | 3180 | 3100 |
| | 1600 | 1690 | 1670 |
| | 785 | 1610 | 1620 |
| | 745 | 795 | 785 |
| | | 785 | 750 |
| | | 750 | |
| | | 735 | |

Differential Calorimetric Analysis

Each polymorph was also characterized by its behaviour under differential characteristic analysis (DCA).

TABLE 2

DCA characteristics of each polymorph:

DCA characteristics

| Anhydrous form | Monohydrate | Trihydrate |
|---|---|---|
| endothermic at 219° C. | endothermic at 170° C. 219° C. | endothermic at 64° C. 103° C. 232° C. |

X-ray Diffraction Pattern of the Powders

The patterns were obtained with Kα radiation of copper at a wavelength λ=1.54 A. In the following table, D and I/I$_1$ represent the inter-reticular spacings and the relative intensities respectively.

TABLE 3

X-ray characteristics of each polymorph:

| Anhydrous | | Monohydrate | | Trihydrate | |
|---|---|---|---|---|---|
| D | I/I$_1$ | D | I/I$_1$ | D | I/I$_1$ |
| 10.99 | 0.92 | 42.44 | 0.20 | 9.18 | 0.669 |
| 8.59 | 0.20 | 12.59 | 0.19 | 7.92 | 0.14 |
| 7.79 | 0.51 | 7.73 | 1.00 | 6.86 | 0.20 |
| 6.09 | 0.55 | 7.00 | 0.19 | 6.10 | 0.29 |
| 5.93 | 0.48 | 6.63 | 0.13 | 5.32 | 0.13 |
| 5.82 | 0.34 | 6.09 | 0.15 | 5.04 | 0.18 |
| 5.29 | 0.24 | 5.93 | 0.16 | 4.79 | 0.17 |

TABLE 3-continued

X-ray characteristics of each polymorph:

| Anhydrous | | Monohydrate | | Trihydrate | |
|---|---|---|---|---|---|
| D | I/I$_1$ | D | I/I$_1$ | D | I/I$_1$ |
| 4.30 | 0.37 | 5.75 | 0.13 | 4.73 | 0.23 |
| 4.20 | 0.28 | 5.63 | 0.13 | 4.59 | 0.18 |
| 3.98 | 0.33 | 5.51 | 0.13 | 4.27 | 0.16 |
| 3.90 | 0.38 | 4.91 | 0.18 | 3.98 | 0.22 |
| 3.72 | 0.84 | 4.52 | 0.17 | 3.83 | 1.00 |
| 3.59 | 1.00 | 4.27 | 0.21 | 3.72 | 0.30 |
| 3.45 | 0.47 | 4.21 | 0.21 | 3.58 | 0.14 |
| 2.88 | 0.31 | 3.90 | 0.22 | 3.49 | 0.74 |
| 2.71 | 0.18 | 3.82 | 0.27 | 3.45 | 0.26 |
| | | 3.75 | 0.27 | 3.34 | 0.66 |
| | | 3.71 | 0.33 | 3.23 | 0.95 |
| | | 3.61 | 0.19 | 3.08 | 0.14 |
| | | 3.51 | 0.36 | 3.06 | 0.14 |
| | | 3.46 | 0.34 | 2.99 | 0.13 |
| | | 3.35 | 0.31 | 2.96 | 0.13 |
| | | 3.32 | 0.20 | 2.82 | 0.13 |
| | | 3.28 | 0.16 | 2.69 | 0.10 |
| | | 3.21 | 0.24 | 2.63 | 0.15 |
| | | 3.14 | 0.23 | 2.60 | 0.17 |
| | | 3.12 | 0.16 | 2.50 | 0.12 |
| | | 3.05 | 0.12 | 2.43 | 0.12 |
| | | 2.90 | 0.13 | | |
| | | 2.80 | 0.14 | | |
| | | 2.68 | 0.11 | | |
| | | 2.64 | 0.12 | | |
| | | 2.60 | 0.13 | | |
| | | 2.50 | 0.14 | | |
| | | 2.45 | 0.10 | | |

Determination of the structure of the trihydrate using X-ray diffraction

It was very difficult to obtain stabilized crystals with 3 molecules of water because already in the atmosphere of the laboratory, the trihydrate naturally loses its hydration water to evolve slowly towards the anhydrous form. Only the preparation of monocrystals of the trihydrated form allowed the presence of 3 molecules of water per mole of zilpaterol hydrochloride (ZC) to be confirmed using X-rays. The crystalline system, the lattice parameters, the space group and the atomic coordinates were thus able to be determined.

| Crystalline system | triclinic |
|---|---|
| a (A) | 8.080 |
| b (A) | 10.268 |
| c (A) | 11.884 |
| alpha (degree) | 113.51 |
| beta (degree) | 90.65 |
| gamma (degree) | 102.34 |
| space group | P1$^-$ |
| Z | 2 |
| R | 6.6 |

Atomic coordinates

| Atom | x/a | y/b | z/c | U(iso) |
|---|---|---|---|---|
| N(3) | 0.4065(4) | 0.2628(4) | −0.0120(3) | 0.0193 |
| C(7) | 0.2882(5) | 0.4401(5) | 0.3820(4) | 0.0201 |
| C(17) | 0.3973(5) | 0.5156(5) | 0.3268(4) | 0.0215 |
| C(15) | 0.3405(5) | 0.3057(5) | 0.1118(4) | 0.0211 |
| C(9) | 0.4474(5) | 0.4538(4) | 0.1967(4) | 0.0206 |
| C(8) | 0.2511(5) | 0.5136(5) | 0.5029(4) | 0.0231 |
| N(4) | 0.2008(5) | 0.2939(4) | 0.3449(3) | 0.0247 |
| O(2) | 0.4486(4) | 0.5546(3) | 0.1403(3) | 0.0235 |

-continued

Atomic coordinates

| Atom  | x/a        | y/b       | z/c        | U(iso) |
|-------|------------|-----------|------------|--------|
| C(11) | 0.1122(6)  | 0.2777(5) | 0.4390(4)  | 0.0280 |
| C(14) | 0.4657(6)  | 0.6642(5) | 0.3992(4)  | 0.0268 |
| C(18) | 0.2821(6)  | 0.1423(5) | −0.1169(4) | 0.0276 |
| C(12) | 0.3426(7)  | 0.1890(5) | 0.1599(4)  | 0.0273 |
| C(21) | 0.3124(6)  | 0.6610(5) | 0.5710(4)  | 0.0297 |
| N(10) | 0.1406(5)  | 0.4126(4) | 0.5330(4)  | 0.0289 |
| C(13) | 0.4260(6)  | 0.7355(5) | 0.5177(4)  | 0.0305 |
| C(23) | 0.1943(7)  | 0.1669(5) | 0.2302(5)  | 0.0319 |
| C(19) | 0.3766(7)  | 0.0613(6) | −0.2193(5) | 0.0372 |
| O(5)  | 0.0251(5)  | 0.1608(4) | 0.4340(3)  | 0.0375 |
| C(20) | 0.1591(7)  | 0.2100(7) | −0.1595(6) | 0.0431 |
| CL(1) | 0.2366(2)  | 0.8016(1) | 0.9663(1)  | 0.0376 |
| O(6)  | 0.2083(4)  | 0.7071(4) | 1.1889(4)  | 0.0390 |
| O(16) | −0.1916(5) | 0.5875(4) | 0.0697(4)  | 0.0497 |
| O(22) | 0.0405(7)  | 0.5001(5) | 0.7688(4)  | 0.0598 |

Conclusions:

The desired granulometry was obtained. 30 kg of premix at 3 percent mass/mass was prepared by the process of European Patent No. 0,197,188 from the product prepared according to process 1. The premix obtained satisfied the Heubach test, which is a well known test, as indicated by Pickard in "Feed Compounder", 1992, p. 18 and subsequent pages.

Heubach test:

Generate dust using a Heubach apparatus modified according to the following conditions: Size of the sample: 50 g of premix; Speed of rotation of the drum: 30 r/m; Duration of rotation: 5 min; Air inlet rate: 4 L/min and Porosity of the filter: 0.45 μm.

The product retained on the filter was then extracted by sonication in methanol and analyzed by HPLC.

Result of the test:<0.1 μg of Zilpaterol per filter.

The Heubach test shows that the crystals were perfectly suitable for the preparation of the premix described in European Patent Application 197,188 to be applied to them.

Various modifications of the product and process of the invention may be made without departing from the spirit or scope thereof and it is to be understood that the invention is intended to be limited only as defined in the appended claims.

What is claimed is:

1. A compound selected from the groups consisting of zilpaterol hydrochloride monohydrate and zilpaterol hydrochloride trihydrate.

* * * * *